US012797491B2

(12) United States Patent
Mordaunt

(10) Patent No.: US 12,797,491 B2
(45) **Date of Patent: *Nov. 17, 2026**

(54) PREFERRED ANTERIOR CAPSULOTOMY LOCATION PROVIDED BY TRYPAN BLUE OPTHALMIC SOLUTION

(71) Applicant: Excel-Lens, Inc., Los Gatos, CA (US)

(72) Inventor: David Mordaunt, Los Gatos, CA (US)

(73) Assignee: EOS Holdings LLC, Los Gatos, CA (US)

( * ) Notice: Subject to any disclaimer, the term of this patent is extended or adjusted under 35 U.S.C. 154(b) by 959 days.

This patent is subject to a terminal disclaimer.

(21) Appl. No.: 17/832,104

(22) Filed: Jun. 3, 2022

(65) Prior Publication Data

US 2022/0362410 A1 Nov. 17, 2022

Related U.S. Application Data

(63) Continuation-in-part of application No. 17/682,711, filed on Feb. 28, 2022, now abandoned, which is a continuation of application No. 15/953,310, filed on Apr. 13, 2018, now Pat. No. 11,260,135.

(60) Provisional application No. 63/197,116, filed on Jun. 4, 2021.

(51) Int. Cl.

| | |
|---|---|
| ***A61K 49/00*** | (2006.01) |
| ***A61B 34/30*** | (2016.01) |
| ***A61F 2/16*** | (2006.01) |
| ***A61F 9/008*** | (2006.01) |
| ***A61K 9/00*** | (2006.01) |
| ***A61K 9/08*** | (2006.01) |

(52) U.S. Cl.

CPC ............ *A61K 49/006* (2013.01); *A61B 34/30* (2016.02); *A61F 2/1662* (2013.01); *A61F 9/008* (2013.01); *A61K 9/0048* (2013.01); *A61K 9/08* (2013.01); *A61B 2218/002* (2013.01); *A61B 2218/007* (2013.01); *A61F 2009/00889* (2013.01)

(58) Field of Classification Search

None

See application file for complete search history.

(56) References Cited

U.S. PATENT DOCUMENTS

| | | | |
|---|---|---|---|
| 6,367,480 | B1 | 4/2002 | Coroneo |
| 6,720,314 | B1 | 4/2004 | Melles |
| 7,731,941 | B2 | 6/2010 | Enaida et al. |
| 11,260,135 | B2 | 3/2022 | Mordaunt |
| 2019/0314529 | A1 | 10/2019 | Mordaunt |
| 2022/0175971 | A1 | 6/2022 | Mordaunt |

OTHER PUBLICATIONS

Chang et al Part I (J Cataract Refract Surg 31:792-798, 2005) (Year: 2005).*

Chang et al Part II (J Cataract Refract Surg 31:799-804, 2005) (Year: 2005).*

Sigma (Trypan Blue Solution 0.4%, available online at https://www.sigmaaldrich.com/US/en/coa/SIGMA/T8154/RNBM1133, accessed Jun. 28, 2025) (Year: 2025).*

Auffarth et al (J Cataract Refract Surg 20:188-191, 1994, Abstract only) (Year: 1994).*

Holland ("Laser Capsulotomy Brings Advantages to Cataract Surgery", available online at https://crstodayeurope.com/articles/2015-oct/continuous-thermal-capsulotomy-a-simple-solution-for-a-longstanding-problem/, Oct. 2015) (Year: 2015).*

Center for Drug Evaluation and Research (NDA Application No. 21-670, 2003) (Year: 2003).*

Morales et al (Invest Ophthamol Vis Sci 51:6018-6029, 2010) (Year: 2010).*

From the USPTO: Non-final Office action corresponding to U.S. Appl. No. 17/682,711, filed Nov. 21, 2023, 13 pages.

Chauhan et al., (J Neurosci Res 66:231-235, 2001) (Year: 2001).

SAFC Biosciences (Trypan Blue Solution 0.4% Product Information, 2006) (Year: 2006).

Brockmann T, Steger C, Dawczynski J. Photodynamic Properties of Vital Dyes for Vitreoretinal Surgery, Ophthalmologica 2012; 228: 234-238.

Melles GR, De Waard PWT, Pameyer JH, et al. Trypan blue capsule staining to visualize the capsulorhexis in cataract surgery. J Cataract Refract Surg 1999;25: 7-9.

Jhanji V, Chan E, Das S, et al. Trypan blue for anterior segment surgeries, Eye (Lond). Sep. 2011; 25(9): 1113-1120.

Rodrigues EB, Costa EF, Penha FM, et al. The Use of Vital Dyes in Ocular Surgery, Survey of Ophth., 54 (5), 576-617 (2009).

Rodrigues EB, Meyer CH, Kroll P. Chromovitrectomy: a new field in vitreoretinal surgery. Graefes Arch Clin Exp Ophthalmol 2005; 243:291-293.

Aguilera Teba F, Mohr A, Eckardt C, et al. Trypan blue staining in vitreoretinal surgery. Ophthalmology 2003; 110:2409-2412.

Sousa-Martins D, Caseli L, Figueiredo M, et al. Comparing the mode of action of intraocular lutein-based dyes with synthetic dyes. IOVS 2015.

Narayanan R, Kenney MC, Kamjoo S, et al. Trypan blue: effect on retinal pigment epithelial and neurosensory retinal cells. Invest Ophthalmol Vis Sci 2005; 46: 304-309.

Jin Y, Uchida S, Yanagi Y, et al. Neurotoxic effects of Trypan blue on rat retinal ganglion cells. Exp Eye Res 2005:81:395-400.

Stalmans P, Van Aken EH, Melles G, et al. Trypan blue not toxic for retinal pigment epithelium in vitro. Am J Ophthalmol 2003; 135: 234-236.

Gale JS, Proulx AA, Gonder JR, et al. Comparison of the in vitro toxicity of indocyanine green to that of Trypan blue in human retinal pigment epithelium cell cultures. Am J Ophthalmol 2004; 138: 64-69.

Mennel S, Thumann G, Peter S, et al. Influence of vital dyes on the function of the outer blood-retinal barrier in vitro. Klin Monatsbl Augenheilkd 2006; 223: 568-576.

(Continued)

*Primary Examiner* — Craig D Ricci

(74) *Attorney, Agent, or Firm* — Schmidt Patent Law, Inc.

(57) ABSTRACT

Trypan Blue ophthalmic solutions are used to create and identify a landmark on the anterior capsule of an eye and thus identify a preferred location for an anterior capsulotomy during cataract surgery.

12 Claims, 8 Drawing Sheets
(3 of 8 Drawing Sheet(s) Filed in Color)

(56) References Cited

OTHER PUBLICATIONS

Kwok AKH, Yeung C-K, Lai TYY, et al. Effects of Trypan blue on cell viability and gene expression in human retinal pigment epithelial cells. Br J Ophthalmol 2004; 88: 1590-1594.
Rezai KA, Farrokh-Siar L, Gasyna EM, et al. Trypan blue induces apoptosis in human retinal pigment epithelial cells. Am J Ophthalmol 2004; 138: 492-495.
Hirasawa H, Yanagi Y, Tamaki Y, et al. Indocyanine green and Trypan blue: intracellular uptake and extracellular binding by human retinal pigment epithelial cells. Retina 2007; 27: 375-378.
Costa E. F, Barros NLT, Coppini LP, et al., Effects of Light Exposure, pH, Osmolarity, and Solvent on the Retinal Pigment Epithelial Toxicity of Vital Dyes, Am J Ophthalmol 2013; 155: 705-712.
Awad D, Schrader I, Bartok M, et al. Comparative toxicology of Trypan blue, brilliant blue G, and their combination together with polyethylene glycol on human pigment epithelial cells. Investigative Ophthalmology & Visual Science 2011; 52(7): 4085-4090.
Costa E.F, et al., Viatal Dyes and Light Sources for Chromovitrectomy: Comparative Assesment of Osmolarity, pH, and Spectrophotometry, Investigative Ophthalmology & Visual Science, Jan. 2009, vol. 50, No. 1, 385-391.
J.P. Graham, et al., Experimental and theoretical study of the spectral behavior of Trypan Blue in various solvents, Journal of Molecular Structure 1040 (2013) 1-8.
Delori et al., Spectral reflectance of the human ocular fundus, Applied Optics, Mar. 15, 1989, vol. 28, No. 6, 1061-1077.
B. Braun Medical, Inc. (available online at https://dailymed.nlm.nih.gov/dailymed/fda/fdaDrugXsl.cfm?setid=f47d4c31-8871-74dd-2e13-52af971a69e0&type=display, Dec. 2018) (Year:2018).
Morales et al., "Comparative Effects of Six Intraocular Vital Dyes on Retinal Pigment Epithelial Cells", IOVS, Nov. 2010, vol. 51, No. 11, pp. 6018-6029.

* cited by examiner

PREFERRED ANTERIOR CAPSULOTOMY LOCATION PROVIDED BY TRYPAN BLUE OPTHALMIC SOLUTION

CROSS-REFERENCE TO RELATED APPLICATIONS

This application is a continuation in part of U.S. patent application Ser. No. 17/682,711 filed Feb. 28, 2022, which is a continuation of U.S. patent application Ser. No. 15/953,310 filed Apr. 13, 2018 (now U.S. Pat. No. 11,260,135). This application also claims benefit of priority to U.S. Provisional Patent Application No. 63/197,116 filed Jun. 4, 2021. Each of the applications identified in this paragraph is incorporated herein by reference in its entirety.

FIELD OF THE INVENTION

The invention relates generally to the use and formulation of Trypan Blue ophthalmic solutions to identify the preferred location of the anterior capsulotomy during cataract surgery.

BACKGROUND

Cataracts are a common cause of poor vision and are the leading cause of blindness. Cataract surgery involves the creation of an approximately circular opening of 4-6 mm diameter in the lens anterior capsule (which is referred to as a capsulotomy or capsulorrhexis), removal of the opacified natural crystalline lens, and insertion of an intraocular lens (IOL) through the capsulotomy into and retained by the remaining lens capsule. Following surgery, the lens capsule contracts over a few months exerting forces on the IOL. Thus, a symmetric anterior capsulotomy about an IOL with 360-degree coverage provides clinical benefits such as minimal early onset posterior capsule opacification (PCO) and minimal IOL tilt and dislocation.

Trypan Blue is a vital dye first synthesized in 1904. Trypan Blue belongs to the anionic diazo family of vital dyes with the chemical formula $C_{34}H_{24}N_6Na_4O_{14}S_4$ and a molecular weight of 960. This organic compound is blue in appearance because red and orange light are strongly absorbed. Trypan Blue dissolved in a neutral pH aqueous solution has its maximum absorption in the orange region of the spectrum at about 590 nm. [1]

Trypan Blue is frequently used in ocular surgery. Since the late 1990s, Trypan Blue with a concentration of equal or less than 0.06% by weight has demonstrated significant affinity properties for the anterior lens capsule and showed an ability to improve visualization by color staining in cataract surgery to facilitate capsulotomy, especially in patients with a white (opaque) cataract.[2-4] Also, vitreoretinal surgeons started the intraoperative application of different dyes to identify membranes and tissues of interest in vitreoretinal surgery. Trypan Blue in a concentration of equal or less than 0.15% is known to effectively stain the glial epiretinal membrane (ERM) in dye enhanced vitreoretinal surgery, also known as chromovitrectomy. [5, 6] No pharmacological, immunological or metabolic means is involved in the Trypan Blue staining process, i.e., no covalent bonds to the dye are formed. [7]

U.S. Pat. No. 6,720,314 to Melles discloses the use of Trypan Blue for visualization during cataract surgery at concentrations of 0.001 to 2.0% with a preferred concentration of 0.1%, and with contrast between stained and unstained tissues based on color. Melles teaches that Trypan Blue does not diffuse into the lens capsule.

U.S. Pat. No. 6,367,480 to Coroneo discloses the use of Trypan Blue for visualization during cataract surgery at concentrations of 0.05 to 3.0% with a preferred concentration of 0.1%, also with contrast between stained and unstained tissues based on color.

U.S. Pat. No. 11,260,135 to Mordaunt discloses the uses of Trypan Blue for optimal visualization during cataract surgery at concentrations of 0.2 to 0.45% for fast and darker staining without the potential of toxicity. For concentrations above this range cell toxicity was noted. A darker stain was disclosed at the boundary of the capsulotomy where the capsulotomy created a rolled over edge of at least twice the thickness as the rest of the capsule. The apparent darkness (reduction in transmitted intensity) of a stained lens capsule tissue increases with the concentration of Trypan Blue in the staining solution and with the thickness of the tissue.

Barraquer et al.[20] describe the finding of their and other studies of human lens capsule thickness measured using photomicroscopy of donor tissue. For patients of mature cataract age (50 years old and greater) the lens capsule on average has relatively uniform thickness from 15 microns at the anterior pole to 17 microns at 5 mm diameter around the pole, then thinning to 7 microns at the equator at about 10 mm diameter. In younger eyes of 30 years old and less, the anterior pole is thinner at about 11 microns.

In the literature, Trypan Blue is only considered to provide a stain of relative uniformity within a single tissue or membrane of relative uniform thickness. There have been no observations or discussions that Trypan Blue solution provides an intense landmark on the anterior capsule. Furthermore, there is no discussion of using Trypan Blue to assist with determining the location of the anterior capsulotomy, identification of the anterior pole of the lens capsule, predicting the IOL resting position, or determination of the visual axis location.

In cataract surgery, identification of the visual axis intersection with the plane of the anterior capsule prior to the capsulotomy can provide the location for centering of the anterior capsulotomy and the geometric foundation for surgery. The IOL location is determined by its haptics centering on the equator of the lens capsular bag, i.e., the IOL is centered on the anterior pole of the lens capsule. It is noted that the IOL position can be fine-tuned, as the IOL can be surgically displaced by up to 300 microns due to resistance between the IOL and capsule. As symmetric coverage of the IOL by the capsulotomy is desired, the location of the anterior capsulotomy in part defines the resting position of the IOL, so placing the capsulotomy in the appropriate position is an essential detail for precise cataract surgery.

There has been a long-standing academic debate regarding whether the anterior capsulotomy should be centered on the limbus center, dilated pupil center, constricted pupil center, optical axis, or visual axis. The optical axis is defined as the geometric center of the cornea. The visual axis is defined as the line of sight from a fixation point to the fovea on the retina, it rarely passes through the constricted pupil center.

Limbus centering is offered by some integrated microscope devices that provide a visual guide for location of the capsulotomy referenced to the limbus. Particular care needs to be taken to avoid intraoperative tilt as the limbus and the anterior capsule are at different depths within the eye, so small degrees of intra-operative patient eye tilt make limbal centration impractical.

Under pharmacological induced mydriasis the pupil dilates asymmetrically; hence the dilated pupil centration does not provide a reliable reference point for either the constricted pupil, optical or visual axis.

Constricted pupil center, optical axis and visual axis are generally considered as valid potential candidates for capsulotomy centration. There are some devices that allow a reference preoperative image or key markers from such an image to be displayed in the surgeon's microscope view and referenced to real-time anatomical landmarks on the iris or sclera blood vessels of the patient's eye [US2011122365A1, US2014118696A1, US2014180162A1]. Some of these devices allow guidance aids for capsulotomy and IOL placement to be displayed aligned with either the constricted pupil center, optical or visual axes. This involves a transfer of patient data between device real-time reference matching. This still does not fully compensate for patient tilt and the 3D nature of the eye, specifically none of the landmarks are in the plane of the anterior capsule.

Femtosecond laser assisted cataract surgery (FLACS) systems [US2006/00873, US2014/0104576, US2021/0077300 A1] disclose the use of OCT imaging technology to 3D map the anterior chamber prior to surgery and allow the capsulotomy to be placed on the dilated pupil center or some calculated axis.

U.S. 202015532A1 to Mordaunt describes a laser cataract system with a blinking fixation light which determines the visual axis of a patient fixated on said light. Pande and Hillman[18] and Erdern [19] utilize coaxially sighted corneal light reflex with the patient fixation to microscope illumination light sources to identify the patient's visual axis for corneal surgery by finding the coaxial Purkinje image that is the reflections from the cornea and anterior capsule are coincident. To use this coaxial Purkinje image, the patient is required to fixate on a light source. This may not always be possible with anesthesia or advanced cataracts.

Accordingly, there is a need in the art to provide new ophthalmic methods, techniques, formulations and devices to advance the standard of care for capsulotomy.

REFERENCES

1. Brockmann T, Steger C, Dawczynski J. Photodynamic Properties of Vital Dyes for Vitreoretinal Surgery, Ophthalmologica 2012; 228: 234-238.

2. Melles G R, De Waard P W T, Pameyer J H, et al. Trypan Blue capsule staining to visualize the capsulorhexis in cataract surgery. J Cataract Refract Surg 1999; 25: 7-9.

3. Jhanji V, Chan E, Das S, et al. Trypan Blue for anterior segment surgeries, Eye (Lond). 2011 September; 25(9): 1113-1120.

4. Rodrigues E B, Costa E F, Penha F M, et al. The Use of Vital Dyes in Ocular Surgery, Survey of Ophth., 54 (5), 576-617 (2009).

5. Rodrigues E B, Meyer C H, Kroll P. Chromovitrectomy: a new field in vitreoretinal surgery. Graefes Arch Clin Exp Ophthalmol 2005; 243:291-293.

6. Aguilera Teba F, Mohr A, Eckardt C, et al. Trypan Blue staining in vitreoretinal surgery. Ophthalmology 2003; 110: 2409-2412.

7. Sousa-Martins D, Caseli L, Figueiredo M, et al. Comparing the mode of action of intraocular lutein-based dyes with synthetic dyes. IOVS 2015.

8. Narayanan R, Kenney M C, Kamjoo S, et al. Trypan Blue: effect on retinal pigment epithelial and neurosensory retinal cells. Invest Ophthalmol Vis Sci 2005; 46:304-309.

9. Jin Y, Uchida S, Yanagi Y, et al. Neurotoxic effects of Trypan Blue on rat retinal ganglion cells. Exp Eye Res 2005:81: 395-400.

10. Stalmans P, Van Aken E H, Melles G, et al. Trypan Blue not toxic for retinal pigment epithelium in vitro. Am J Ophthalmol 2003; 135: 234-236.

11. Gale J S, Proulx A A, Gonder J R, et al. Comparison of the in vitro toxicity of indocyanine green to that of Trypan blue in human retinal pigment epithelium cell cultures. Am J Ophthalmol 2004; 138: 64-69.

12. Mennel S, Thumann G, Peter S, et al. Influence of vital dyes on the function of the outer blood-retinal barrier in vitro. Klin Monatsbl Augenheilkd 2006; 223: 568-576.

13. Kwok A K H, Yeung C-K, Lai T Y Y, et al. Effects of Trypan Blue on cell viability and gene expression in human retinal pigment epithelial cells. Br J Ophthalmol 2004; 88: 1590-1594.

14. Rezai K A, Farrokh-Siar L, Gasyna E M, et al. Trypan Blue induces apoptosis in human retinal pigment epithelial cells. Am J Ophthalmol 2004; 138: 492-495.

15. Hirasawa H, Yanagi Y, Tamaki Y, et al. Indocyanine green and Trypan Blue: intracellular uptake and extracellular binding by human retinal pigment epithelial cells. Retina 2007; 27: 375-378.

16. Costa E. F, Barros N L T, Coppini L P, et. Al., Effects of Light Exposure, pH, Osmolarity, and Solvent on the Retinal Pigment Epithelial Toxicity of Vital Dyes, Am J Ophthalmol 2013; 155: 705-712.

17. Awad D, Schrader I, Bartok M, et al. Comparative toxicology of Trypan Blue, brilliant blue G, and their combination together with polyethylene glycol on human pigment epithelial cells. Investigative Ophthalmology & Visual Science 2011; 52(7): 4085-4090.

18. Pande M, Hillman J S. Optical zone centration in keratorefractive surgery. Entrance pupil center, visual axis, coaxially sighted corneal reflex, or geometric corneal center?. Ophthalmology. 01993; 100:1230-1237

19. Erdem U et al. Pupil Center Shift Relative to the Coaxially Sighted Corneal Light Reflex Under Natural and Pharmacologically Dilated Conditions J. Refrac. Surg. 2008; 24;530-8

20. Barraquer R I et al. Human lens capsule thickness as a function of age and location along the sagittal lens perimeter. Invest Ophthalmol Vis Sci. 2006; 47:2053-60.

SUMMARY

The inventor has discovered that certain formulations of Trypan Blue ophthalmic solution may be used to identify the preferred anterior capsulotomy location during cataract surgery. In particular, the inventor has discovered that Trypan Blue solutions of specific formulations applied into the anterior chamber result in a Trypan Blue Capsular (TC) landmark, a visibly intense blue stained region of the anterior capsule with a diameter of 2 to 4 mm centered or approximately centered on the intersection of the visual axis and the anterior capsule. A capsulotomy centered on this TC landmark is thus centered or approximately centered on the intersection of the visual axis and the capsule. A symmetric anterior capsulotomy about an IOL centered on the visual axis with 360-degree coverage provides clinical benefit.

The inventor has further determined the formulation range that provides a practical waiting time to achieve fast and visible TC landmarks on the anterior capsule.

In one aspect, an ophthalmic solution for use in creating a TC landmark during cataract surgery comprises an isotonic and pH neutral aqueous solution of Trypan Blue at a concentration of 0.25 to 0.45% by weight. The solution may be contained in a delivery device, such as for example a syringe. The solution may be applied to the lens capsule through the delivery device to identify the preferred location of the anterior capsulotomy.

In another aspect, the center of the TC landmark corresponds to the close vicinity (within 200 microns) of the visual axis intersection with the anterior capsule.

In the above invention, the TC landmark corresponds to the anterior pole of the lens capsule, i.e., the resting position of an IOL following implantation.

In the above method, this formulation of Trypan Blue solution is applied to the anterior capsule to stain tissues. The anterior pole of the capsule may be distinguished from surrounding anterior capsule tissues by the intensity of light transmitted through the tissues, for example by the intensity of red light reflected from the retina and transmitted through the lens capsule, in addition to or instead of by differences in the color between stained and unstained tissue. This enhances visualization of the anterior pole of the capsule compared to prior art methods which do not observe or discuss a TC landmark within the anterior capsule. The size of the TC landmark ranges between 2 and 4 mm in diameter and does not correspond with the reported lens capsule thickness which has a maximum at 5 mm [Barraquer].

This formulation and method of forming the TC landmark can be used with any method of capsulotomy including manual capsulorrhexis, laser capsulotomy, and machine vision guided capsulotomies that detect the TC landmark and center an automated capsulotomy about the detected TC landmark.

The inherent advantages of this method and formulation are four-fold. First, that the resultant TC landmark is in the plane of the anterior capsule and capsulotomy, thus it is independent for patient eye tilt. Second, it does not rely upon patient involvement and cooperation such as fixation methods or devices, which may be limited by sedation preventing the patient from cooperating and/or fixating on a light source. Third, it does not require complex imaging devices in the operating room. Fourth, data transfer of preoperative images is not required.

These and other embodiments, features, and advantages of the present invention will become more apparent to those skilled in the art when taken with reference to the following more detailed description of the invention in conjunction with the accompanying drawings that are first briefly described.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION

The following detailed description should be read with reference to the drawings, in which identical reference numbers refer to like elements throughout the different figures. The drawings, which are not necessarily to scale, depict selective embodiments and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives, and uses of the invention, including what is presently believed to be the best mode of carrying out the invention.

As used in this specification and the appended claims, the singular forms "a," "an," and "the" include plural referents unless the context clearly indicates otherwise.

Figures 1A, 1B, 1C:
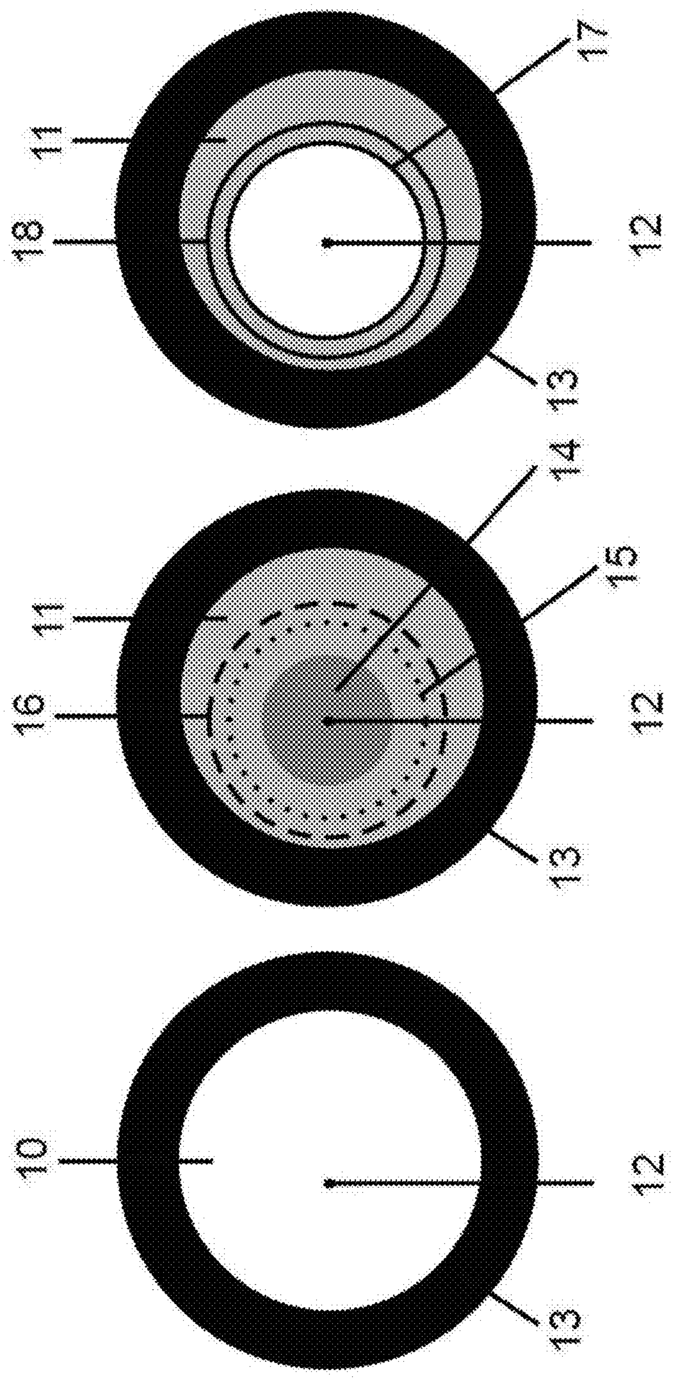
FIGS. 1A, 1B, and 1C illustrate the anatomy of the eye in anteroposterior (AP) view with the visual axis intersection of the anterior capsule, TC landmark, planned capsulotomy location, and predicted IOL location.
Figures 2A, 2B, 2C, 2D, 2E, 2F:
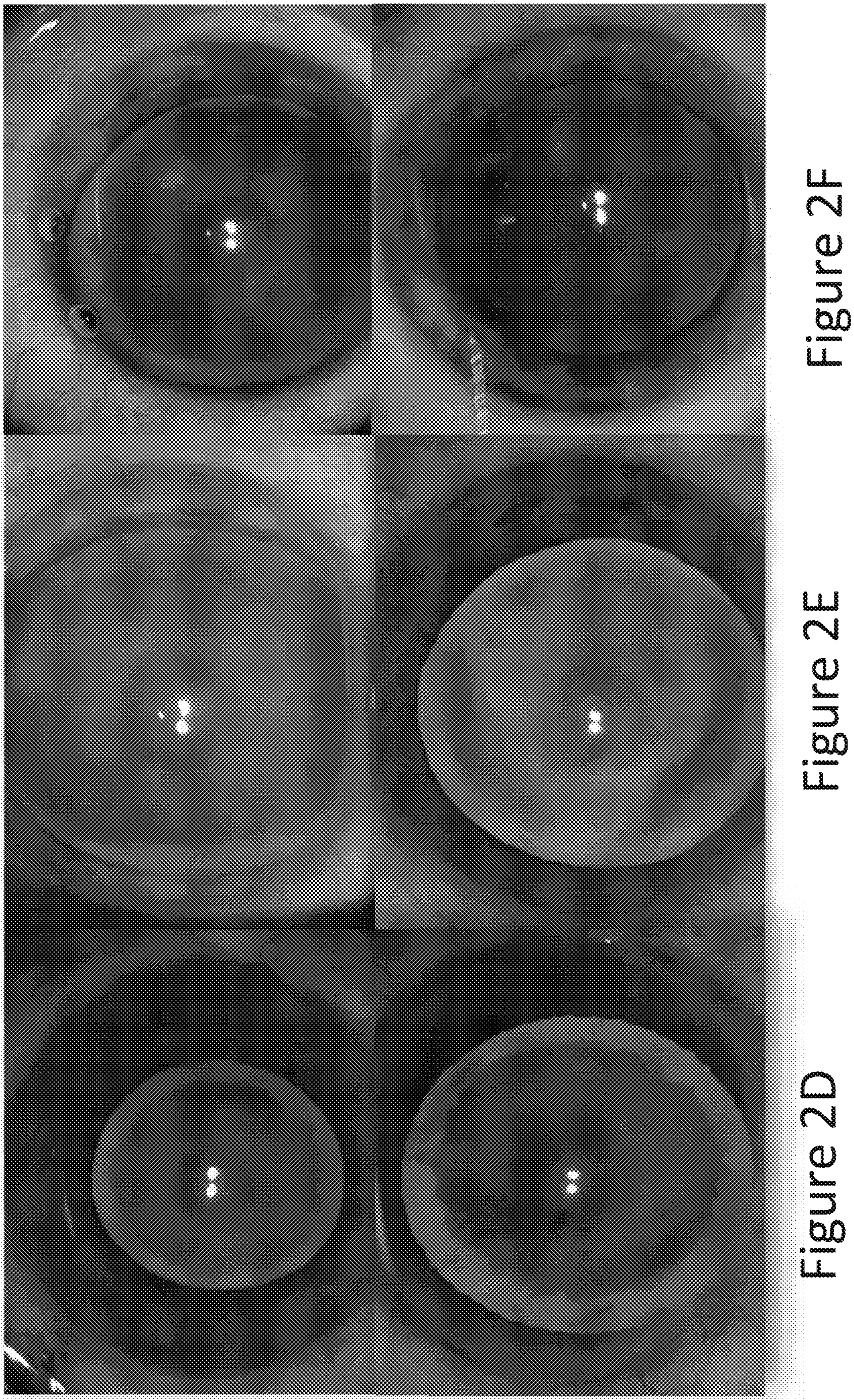
FIGS. 2A, 2B, 2C, 2D, 2E, and 2F are photographs demonstrating the TC landmark on patient eyes.

FIGS. 1A-1C illustrate the anatomy of the eye in an Anterior-Posterior orientation. FIG. 1A is a representation of an eye showing an unstained anterior capsule 10, the point of intersection 12 of the visual axis and the anterior capsule, and the iris 13.

FIG. 1B is a representation of an eye showing a dye-stained capsule 11 stained with the Trypan Blue ophthalmic solution and the method described above, the resulting TC landmark 14 centered on the point of intersection 12 of the visual axis and the anterior capsule, the planned position 15 for a capsulotomy centered on the TC landmark and the intersection 12 of the visual axis and the anterior capsule, the predicted IOL resting position 16, and the iris 13. The stained TC landmark 14 is noticeably darker (less light intensity) than the surrounding stained capsule, which increases the visibility of the TC landmark 14.

FIG. 1C is a representation of an eye showing the dye-stained anterior capsule 11 stained with the Trypan Blue ophthalmic solution and the method described above, the rim 17 of a capsulotomy centered on the intersection 12 of the visual axis and the anterior capsule, an IOL optics body 18 positioned within the capsule and centered on the rim 17 of the capsulotomy and the intersection 12 of the visual axis and the anterior capsule, and the iris 13.

FIGS. 2A-2F are a series of six representative photographs of eyes in which the anterior lens capsule has been stained with the Trypan Blue ophthalmic solution as described above. The TC landmarks are the dark intense stain regions on the anterior capsule. These patients are fixated on the microscope illumination lights and the coaxial Purkinje images are present and denoted by the two light reflections at the center of the TC landmarks.

The inventor has experimentally determined that the threshold for the TC landmark is 0.25% or greater concentration of Trypan Blue ophthalmic solution for a staining duration of at least 90 seconds. For higher concentrations the required staining duration is less. For example with a 0.3% solution the required staining duration is at least 75 seconds, with a 0.35% solution the required staining duration is at least 60 seconds, and with a 0.4% solution the required staining duration is at least 45 seconds, to observe the TC landmarks in the vast majority of cases.

It is noteworthy that porcine eyes do not readily show a TC landmark. Experimental work was conducted in human clinical studies of over 150 eyes. Over 94% of eyes demonstrated the presence of a TC landmark when stained with the Trypan Blue ophthalmic solution. The size of the landmark varied from 2 to 4 mm. On the patients that did not have a visible TC landmark for a 60 second stain, more dye was applied to the anterior chamber and the staining process was repeated. The TC landmark then became visible on all patients, indicating the more concentrated solution and longer staining durations have the benefit of enhancing the visibility of the TC landmark.

The inventor has conducted additional research to determine the mechanism of action for the formation of the TC landmark and has observed that the central zone of the capsule is more porous than the surrounding peripheral region. Furthermore, the lens epithelial cells that are posterior to the anterior capsule have a different structure and function in this central zone compared to the peripheral zone. That is, in the central zone the cells are larger cuboids and one of their main functions is to pump fluids and nutrients from the anterior chamber into the lens capsule. The Trypan Blue molecule is small compared to the pores in the collagen anterior capsule and is absorbed into the capsule in this central region. The highly stained central region at the anterior pole is probably the result of the increased surface area of the pores and the pump action of the epithelial cells.

Figure 3:
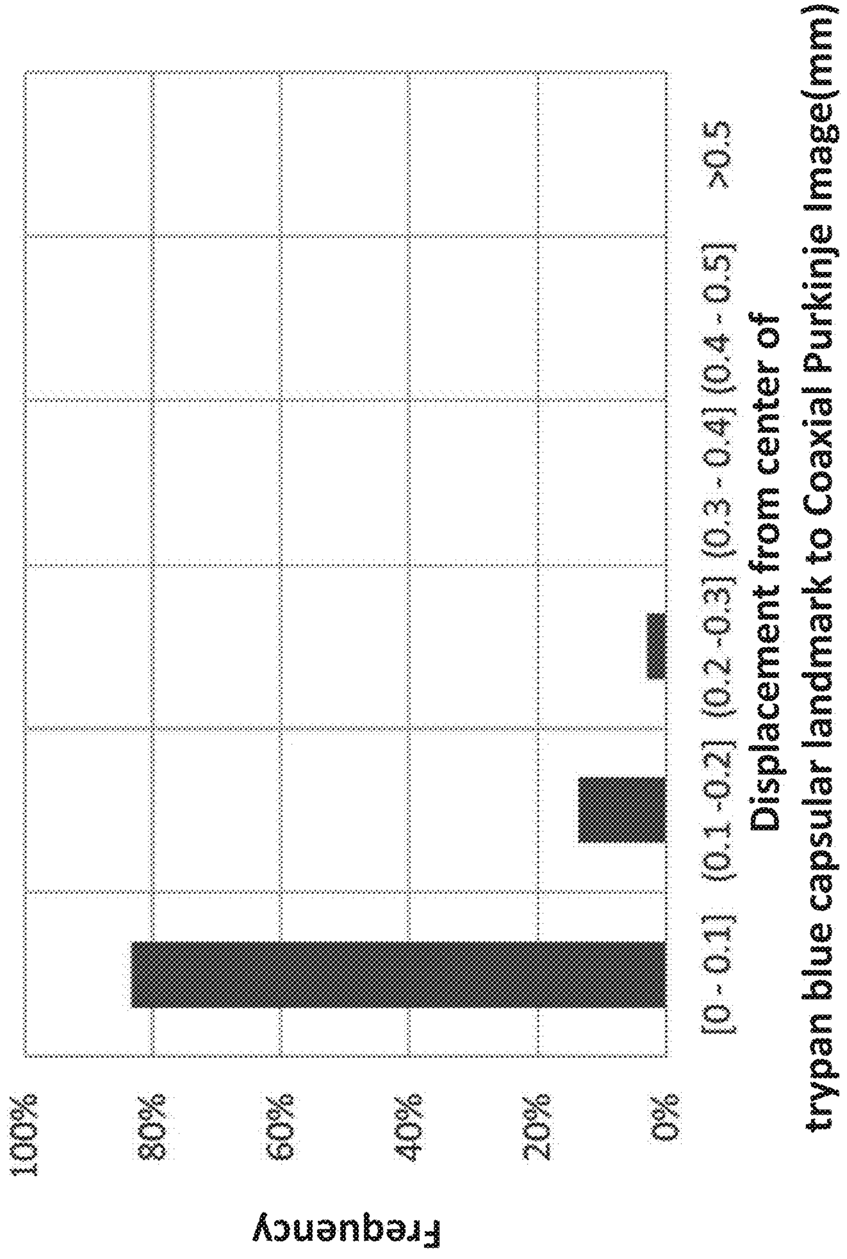
FIG. 3 is a bar chart distribution of displacement from the TC and coaxial Purkinje image.
Figures 4A, 4B, 4C, 4D, 4E, 4F:
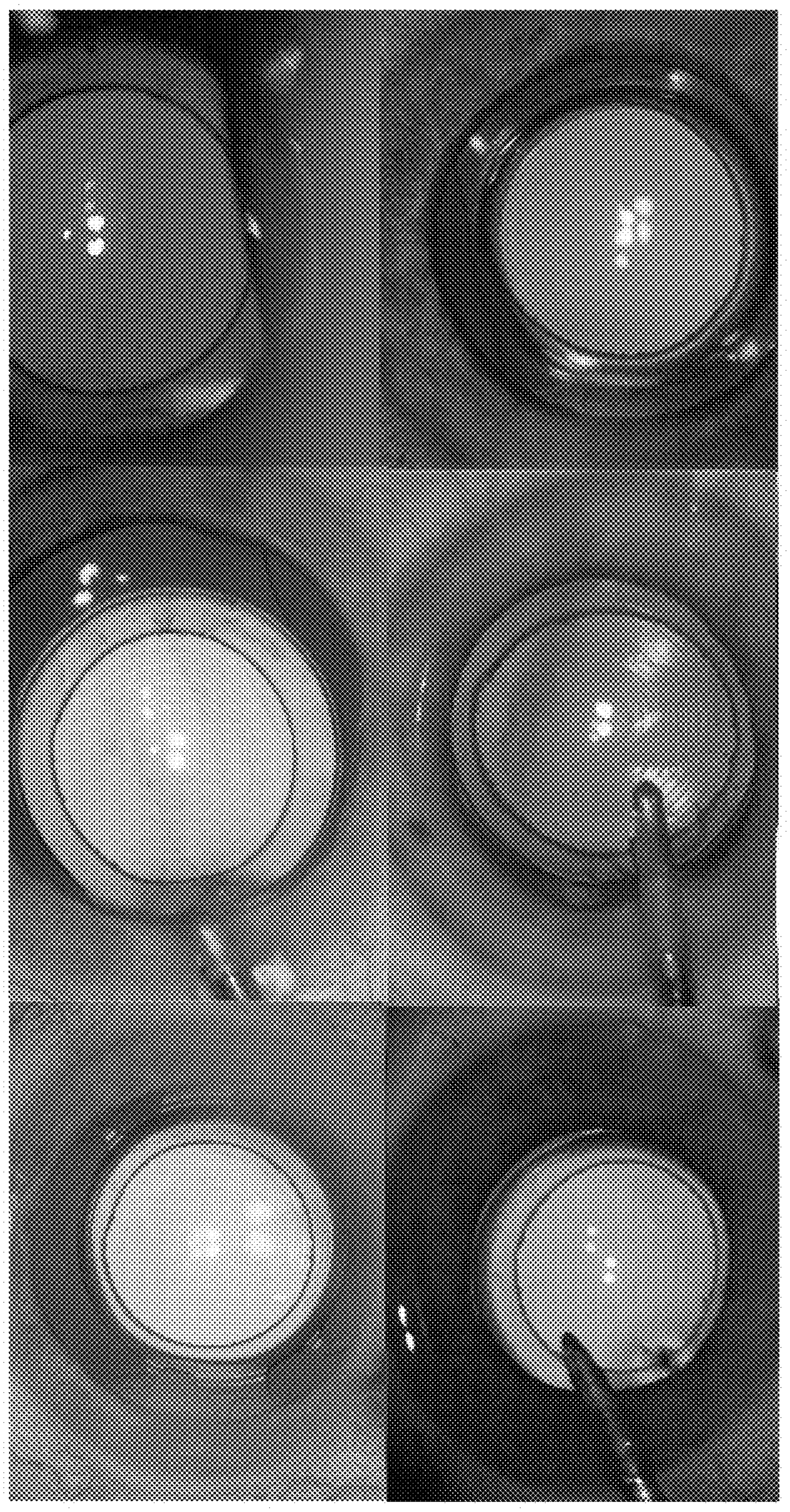
FIGS. 4A, 4B, 4C, 4D, 4E, and 4F are photographs demonstrating capsulotomies centered on the TC landmarks.

FIG. 3 reports the displacement from the TC landmarks to the sighted fixation coaxial Purkinje image. In all eyes the correlation between the TC landmark and coaxial Purkinje images are within 0.3 mm, and over 80% are within 0.1 mm. The coaxial Purkinje image is a good measurement of the visual axis intercept with the anterior capsule. The Zeiss IOLMaster 700 was also used to measure the preoperative visual axis and this reference image was imported into the Zeiss CALLISTO-eye® system, matched to the sclera vessels and confirmed the results of the Purkinje image measurements with the same tolerances.

FIGS. 4A-4F are a series of six representative photographs of eyes following capsulotomies centered on the TC landmark and IOL insertion. Again, the patient eyes are fixated on the microscope illumination lights and the coaxial Purkinje images are present and denoted by the two light reflections at the center of the IOLs.

Figure 5:
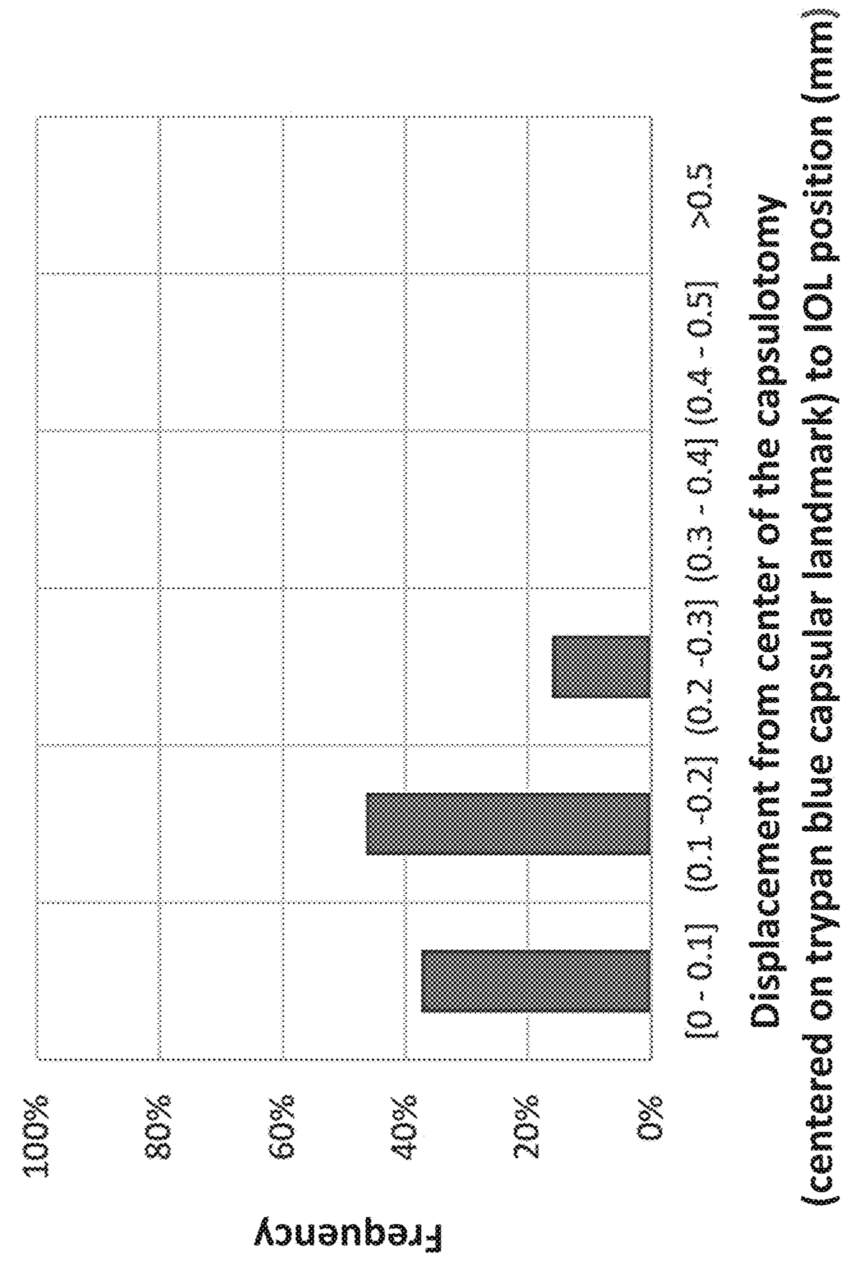
FIG. 5 is a bar chart distribution of displacement from the center of the capsulotomy to the coaxial Purkinje image.
Figure 6:
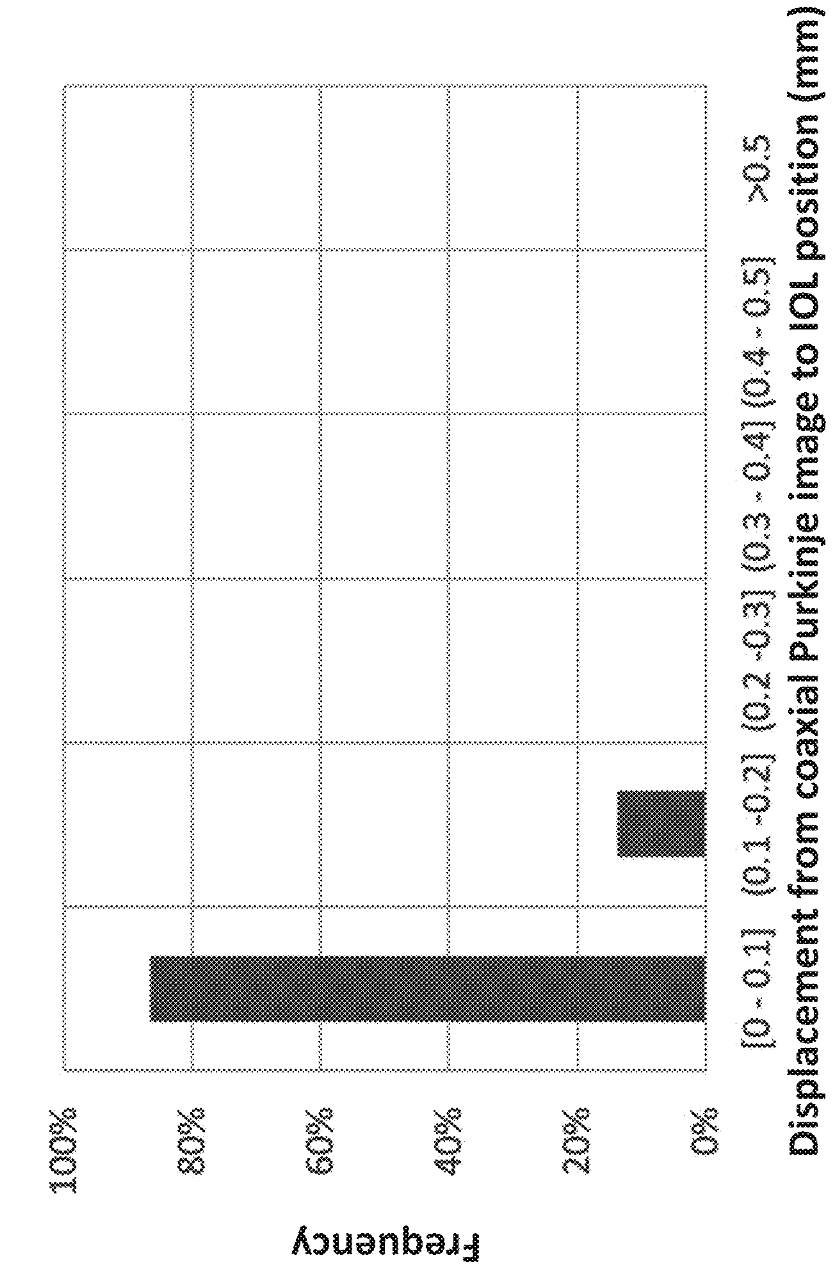
FIG. 6 is a bar chart distribution of displacement from the center of the IOL to the coaxial Purkinje image.

Referring to FIG. 5, the inventor has experimentally determined that capsulotomies centered on the TC landmark are highly correlated with the visual axis intersection with the anterior capsulotomy. All capsulotomies are within 0.3 mm of the coaxial Purkinje image and over 80% are within 0.2 mm. As before the Zeiss IOLMaster visual axis reference image was imported in the Zeiss CALLISTO-eye® and confirmed the results of the Purkinje image measurements with the same tolerances for these capsulotomies. As shown in FIG. 6, the IOLs could all be positioned within 0.3 mm of the capsulotomy centers and within 0.2 mm of the coaxial Purkinje images.

Figure 7B:
FIGS. 7A and 7B are photographs showing the results if capsulotomies are located on the dilated pupil.
Figure 7A:
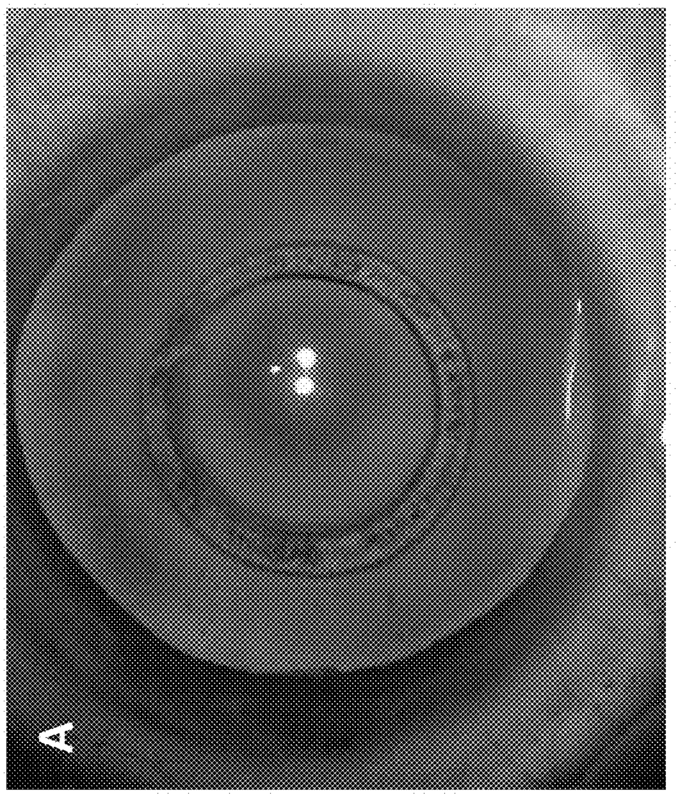

As a control, 50 eyes were dilated, then stained with Trypan Blue ophthalmic solution, and the capsulotomies located on the dilated pupil centers. FIG. 7A shows-the results with a capsulotomy centered on the dilated pupil. The capsulotomy disc is still present, and the TC and coaxial Purkinje images are to the nasal (right) side of the pupil centered capsulotomy. FIG. 7B shows that the IOL does not follow the capsulotomy, but is also displaced to the nasal side following the TC and coaxial Purkinje images. In these cases, the maximum capsulotomy displacement from the IOL center was 0.6 mm and the capsulotomy is not symmetrically capturing the IOL. This highlights the need for accurate location of the anterior capsulotomy, such as facilitated by the invention disclosed in this patent.

Figure 8:
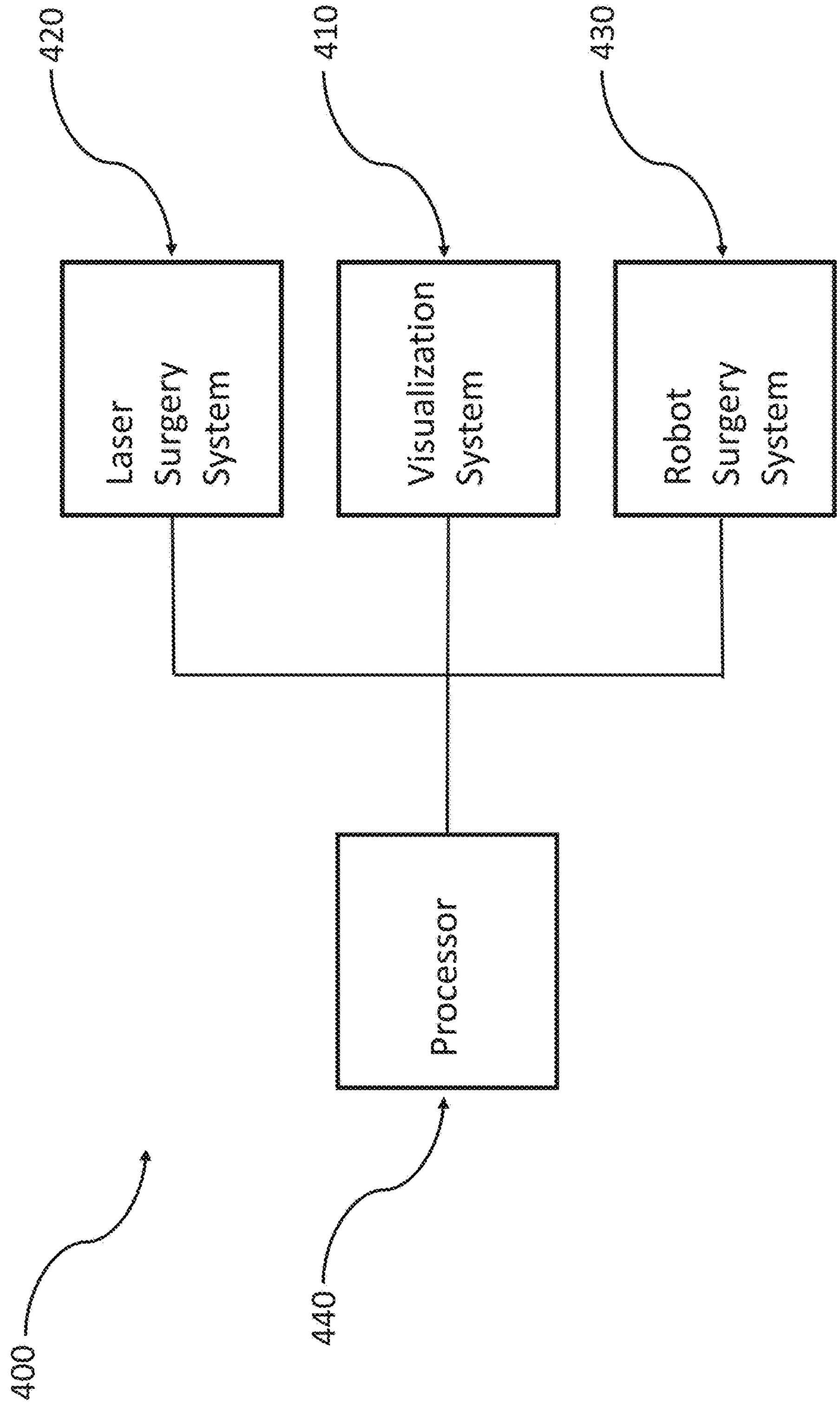
FIG. 8 shows a schematic diagram of an example cataract surgery system.

FIG. 8 shows a schematic diagram of an example cataract surgery system 400 that may be employed with the dye solutions and related methods described herein with visualization of the TC landmark. System 400 comprises a visualization system 410, an optional surgical laser system 420, an optional robot surgical system 430, and an optional processor 440. Visualization system 410 may be used by a human surgeon or by a robotic surgical system to view the lens capsule and other portions of the surgical field during cataract surgery. Visualization system 410 may comprise, for example, a stereoscopic microscope as conventionally employed in ophthalmic surgery, an imaging system including a camera or other imaging device, or a microscope and a camera or other imaging device. In variations in which cataract surgery is performed using laser ophthalmic surgical methods, system 400 may comprise an optional ophthalmic surgical laser system 420. Portions of the optical path of surgical laser system 420, if present, may optionally be integrated into an optical path of visualization system 410. In variations in which cataract surgery is robotically assisted or performed, system 400 may comprise robot surgical system 430 which may perform as described above, for example. System 400 may comprise a processor 440 in communication with any or all of visualization system 410, laser system 420, and robot surgical system 430. Processor 440 may, for example, collect and analyze images from the visualization system, analyze them as described above, and control laser system 420 and/or robot surgical system 430 to assist or perform cataract surgery.

This disclosure is illustrative and not limiting. Further modifications will be apparent to one skilled in the art in light of this disclosure and are intended to fall within the scope of the appended claims.

What is claimed is:

1. A method for creating and identifying a landmark on the anterior lens capsule of the eye during cataract surgery, the method comprising:

applying an ophthalmic solution comprising an isotonic and PH neutral aqueous solution of Trypan Blue at a concentration of greater than or equal to 0.3% and less than or equal to 0.45% by weight to the anterior lens capsule for a time period of less than or equal to one hundred seconds to stain tissue of the anterior lens capsule with Trypan Blue;

rinsing the ophthalmic solution from the eye; and after rinsing the ophthalmic solution from the eye, identifying as the landmark a central region of anterior lens capsule tissue that is more darkly stained with Trypan Blue than surrounding anterior lens capsule tissue stained with Trypan Blue;

wherein the central region of anterior lens capsule tissue that is more darkly stained with Trypan Blue than surrounding anterior lens capsule tissue stained with Trypan Blue has a diameter of about 2 mm to about 4 mm.

2. The method of claim 1, wherein the concentration of Trypan Blue is greater than or equal to 0.35% and less than or equal to 0.45% by weight.

3. The method of claim 1, wherein the concentration of Trypan Blue is greater than or equal to 0.4% and less than or equal to 0.45% by weight.

4. The method of claim 1, comprising identifying the landmark on the anterior lens capsule utilizing machine vision.

5. A method for replacing the natural crystalline lens of an eye with an IOL during cataract surgery, the method comprising:

creating and identifying a landmark on an anterior lens capsule of the eye by the method of claim 1;

forming an opening in the anterior lens capsule centered on the landmark;

removing the natural crystalline lens through the opening in the anterior lens capsule; and inserting the IOL into the anterior lens capsule through the opening in the anterior lens capsule.

6. The method of claim 5, wherein the opening formed in the anterior lens capsule is symmetric.

7. The method of claim 5, comprising centering the IOL on the opening in the anterior lens capsule.

8. The method of claim 5, wherein a center point of the landmark identifies a resting position of a center of the IOL to within about 300 microns.

9. The method of claim 5, wherein the concentration of Trypan Blue is greater than or equal to 0.35% and less than or equal to 0.45% by weight.

10. The method of claim 5, wherein the concentration of Trypan Blue is greater than or equal to 0.4% and less than or equal to 0.45% by weight.

11. The method of claim 5, comprising identifying the landmark on the anterior lens capsule utilizing machine vision.

12. The method of claim 1, wherein the eye is a human eye.

* * * * *